US011116256B1

(12) United States Patent
Fujita et al.

(10) Patent No.: US 11,116,256 B1
(45) Date of Patent: Sep. 14, 2021

(54) INHALATION DEVICE CONTROLLER

(71) Applicant: Japan Tobacco Inc., Tokyo (JP)

(72) Inventors: Noritoshi Fujita, Tokyo (JP); Takeshi Akao, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 17/191,706

(22) Filed: Mar. 4, 2021

(30) Foreign Application Priority Data

Mar. 10, 2020 (JP) .............................. JP2020-041173

(51) Int. Cl.
 *A24F 40/53* (2020.01)
 *A24F 40/42* (2020.01)
(52) U.S. Cl.
 CPC .............. *A24F 40/53* (2020.01); *A24F 40/42* (2020.01)
(58) Field of Classification Search
 None
 See application file for complete search history.

(56) References Cited

U.S. PATENT DOCUMENTS

| 9,814,263 | B2 * | 11/2017 | Cochand ................. A24F 40/53 |
| 2014/0020693 | A1 | 1/2014 | Cochand et al. |
| 2017/0135406 | A1 * | 5/2017 | Reevell .................... H05B 3/04 |
| 2017/0258137 | A1 * | 9/2017 | Smith .................. H05B 1/0244 |
| 2020/0196672 | A1 | 6/2020 | Mizuguchi et al. |

FOREIGN PATENT DOCUMENTS

| JP | 5999716 | B2 | 9/2016 |
| JP | 6553799 | B1 | 7/2019 |
| JP | 2020-5602 | A | 1/2020 |
| JP | 6636198 | B1 | 1/2020 |
| JP | 2020-171254 | A | 10/2020 |
| WO | 2019/082280 | A1 | 5/2019 |
| WO | 2019/082282 | A1 | 5/2019 |

OTHER PUBLICATIONS

Notice of Reasons for Refusal dated Jun. 8, 2020, received for JP Application 2020-041173, 5 pages including English Translation.
Decision to Grant dated Aug. 11, 2020, received for JP Application 2020-041173, 5 pages including English Translation.
Extended European Search Report dated Aug. 5, 2021 in European Patent Application No. 21159887.5, 8 pages.

\* cited by examiner

*Primary Examiner* — James Harvey
(74) *Attorney, Agent, or Firm* — Xsensus LLP

(57) ABSTRACT

An inhalation device controller includes a holder that holds an atomizer including a heater for atomizing an aerosol source, and a processor. Upon detecting an atomization request, the processor executes first determination processing of determining a remaining amount of the aerosol source in the atomizer using a first algorithm, and upon detecting an atomization request after the execution of the first determination processing, executes second determination processing of determining presence/absence of the aerosol source in the atomizer using a second algorithm. Even if it is determined by the first determination processing that the remaining amount is larger than 0, if aerosol source absence is determined by the second determination processing, the processor outputs the aerosol source absence as a final determination result, and inhibits a supply of power to the heater.

4 Claims, 10 Drawing Sheets

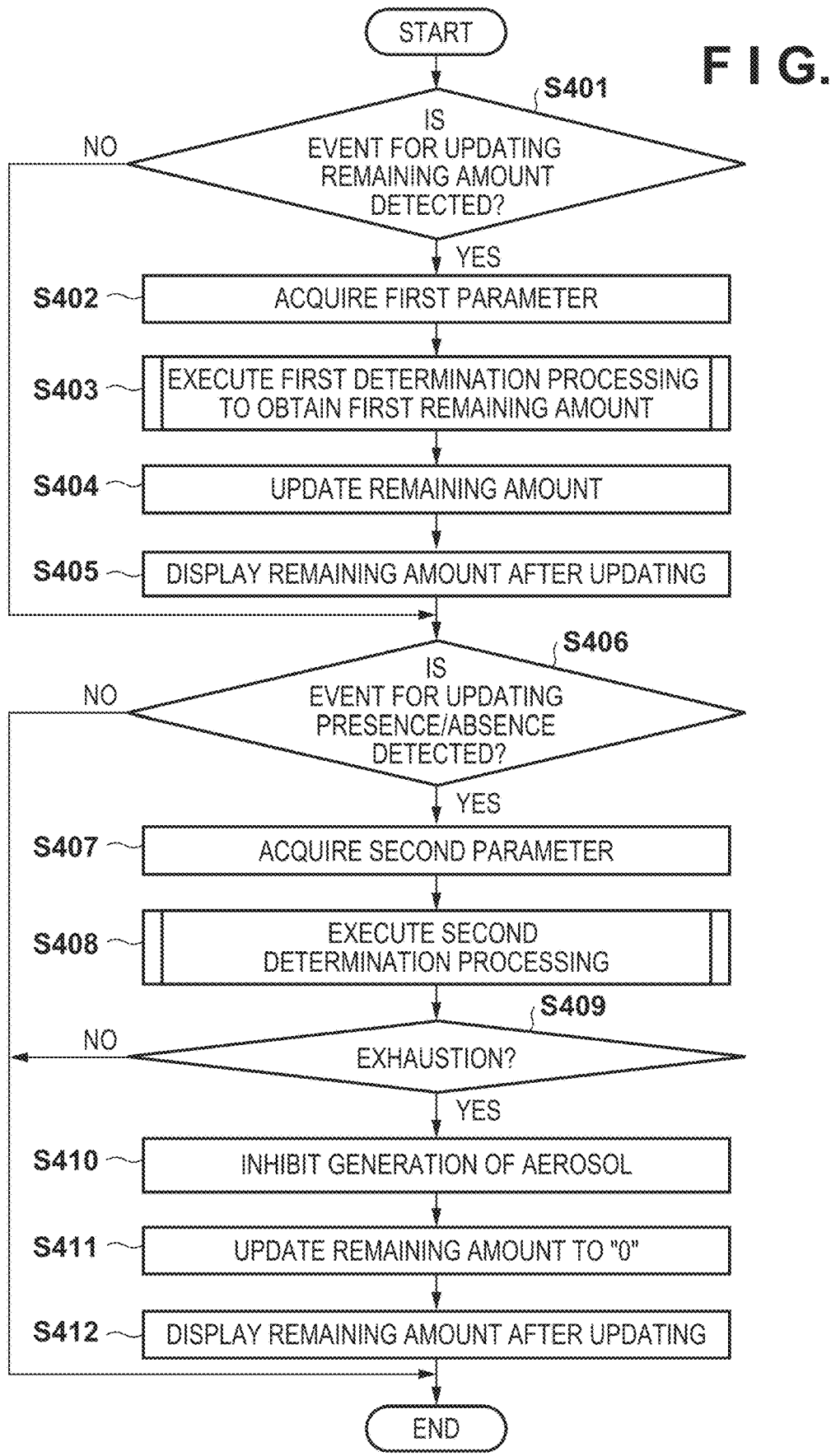

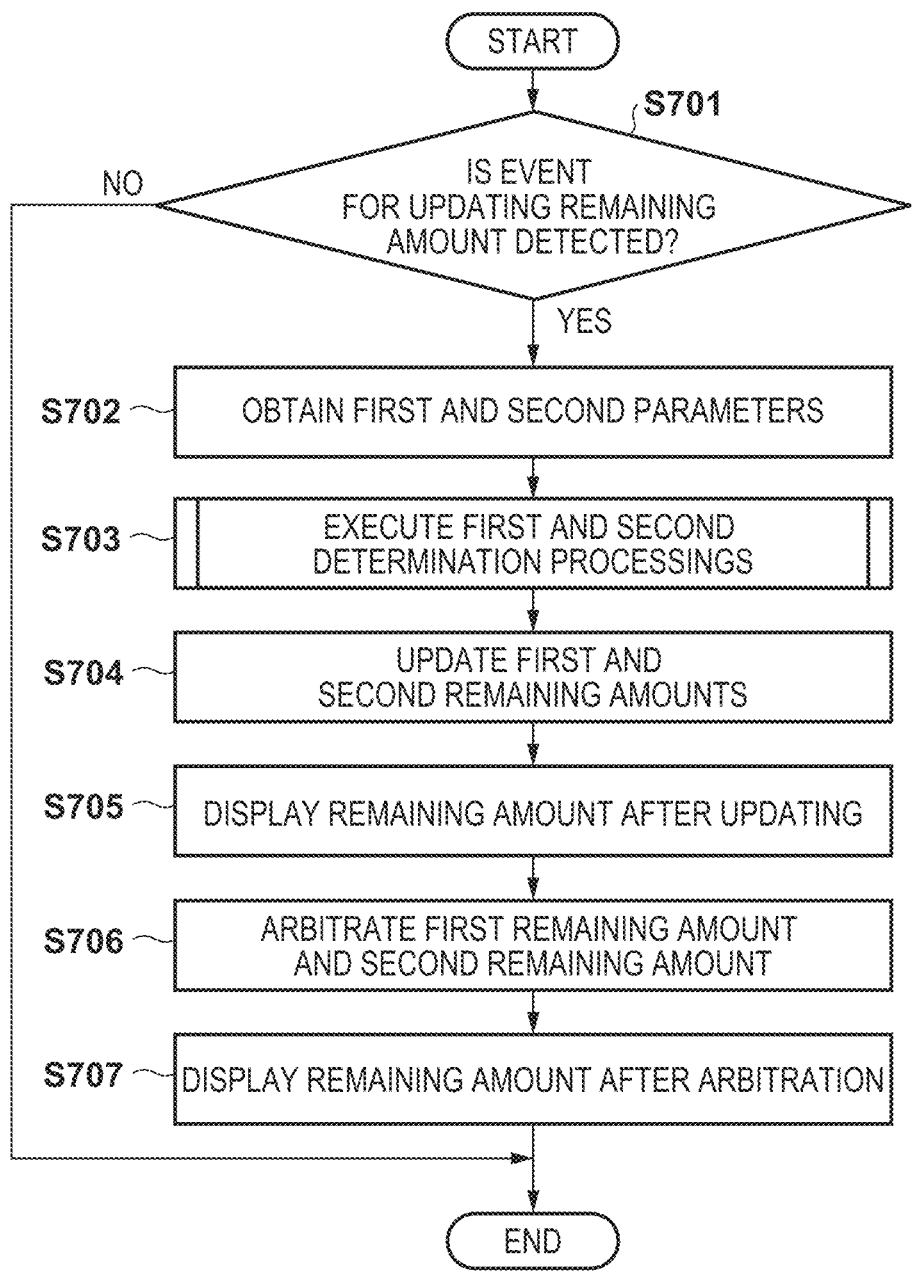

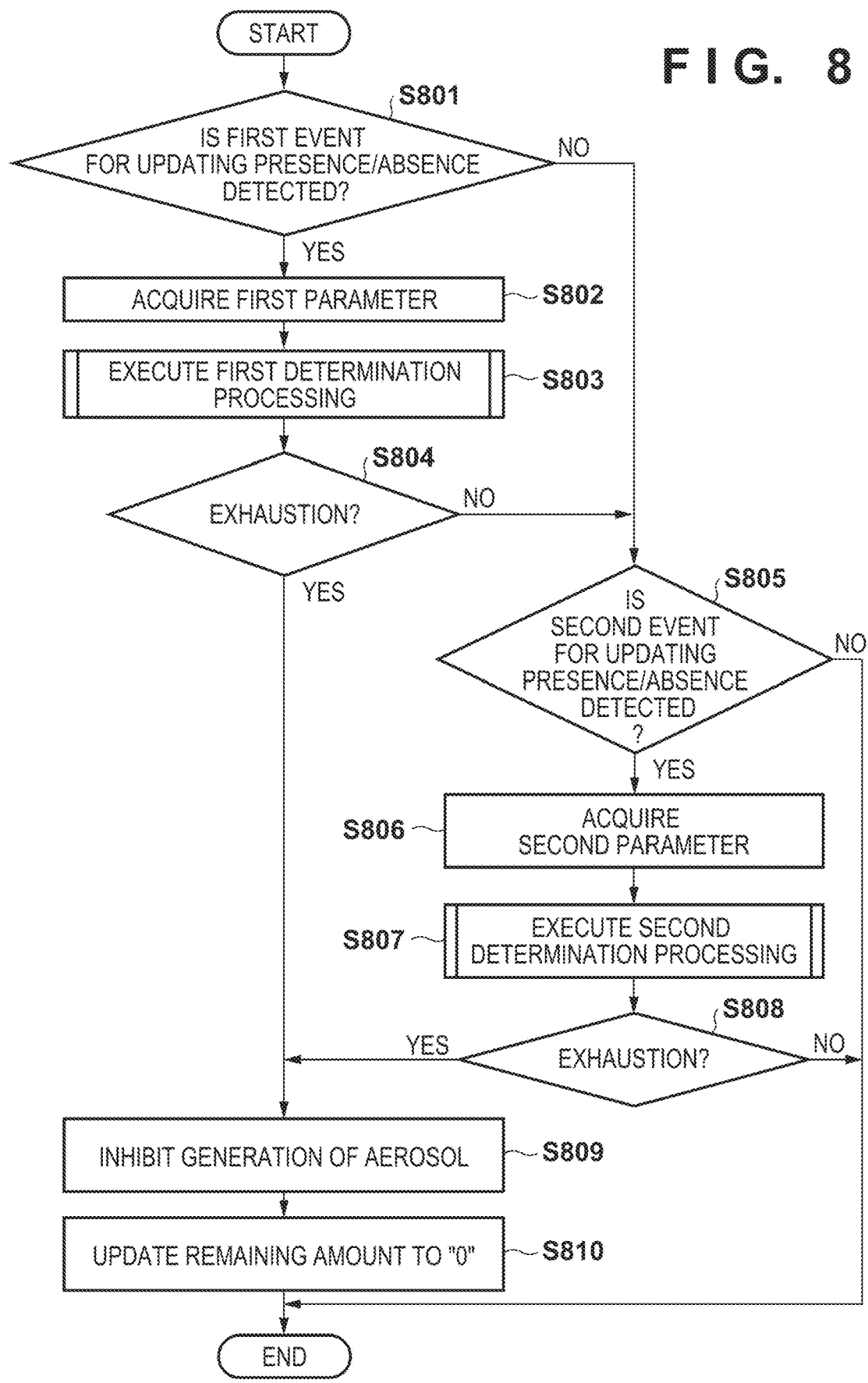

INHALATION DEVICE CONTROLLER

CROSS-REFERENCE TO RELATED APPLICATION

The present invention contains subject matter related to Japanese Patent Application No. 2020-041173 filed in the Japan Patent Office on Mar. 10, 2020, the entire contents of which are incorporated herein by reference.

BACKGROUND OF THE INVENTION

Field of the Invention

The present invention relates to an inhalation device controller.

Description of the Related Art

In an inhalation device configured to generate an inhalable aerosol, an atomizer that holds an aerosol source and atomizes the aerosol source can be configured to be exchangeable. If the aerosol source in the atomizer has run out, the atomizer is exchanged with a new atomizer. Hence, if it is possible to obtain information concerning the remaining amount of the aerosol source in the atomizer, a user can know an atomizer exchange timing in advance, and it is possible to avoid abrupt running out of the aerosol source for the user. In addition, if information concerning the presence/absence of the aerosol source in the atomizer can be obtained, it is possible to prevent a situation in which an atomization operation is performed in a state in which the aerosol source in the atomizer has run out.

Conventionally, there have been proposed various methods of determining the presence/absence or the remaining amount of an aerosol source. For example, Japanese Patent No. 6553799 discloses a technique of determining the presence/absence of an aerosol source based on the temperature of a heater for atomizing the aerosol source or the rising speed of the temperature. Also, Japanese Patent No. 5999716 discloses a technique of determining the remaining amount of an aerosol source based on the relationship between power supplied to a heater for atomizing the aerosol source and a change in the temperature of the heater.

Accurately and inexpensively implementing a mechanism configured to determine the presence/absence or the remaining amount of an aerosol source is an important requirement in increasing the convenience and safety of an inhalation device.

SUMMARY OF THE INVENTION

The present invention provides a technique advantageous in, for example, increasing the accuracy of determining the presence/absence or the remaining amount of an aerosol source.

The present invention in its first aspect provides an inhalation device controller comprising a holder configured to hold an atomizer including a heater for atomizing an aerosol source, and a processor configured to execute, upon detecting an atomization request, first determination processing of determining a remaining amount of the aerosol source in the atomizer held by the holder using a first algorithm, and execute, upon detecting an atomization request after the execution of the first determination processing, second determination processing of determining presence/absence of the aerosol source in the atomizer using a second algorithm different from the first algorithm, and control a supply of power to the heater, and a memory configured to store a value of the remaining amount of the aerosol source in the atomizer, wherein even if it is determined by the first determination processing that the remaining amount is larger than 0, if aerosol source absence is determined by the second determination processing, the processor outputs the aerosol source absence as a final determination result, and inhibits the supply of power to the heater and updates the value in the memory to 0 according to the final determination result.

According to an embodiment, the atomizer further comprises a container configured to hold the aerosol source, and a transporter configured to transport the aerosol source in the container to a position at which the aerosol source can be heated by the heater, a variable necessary for executing the first determination processing is acquired from one element of the heater, the container, and the transporter, and a variable necessary for executing the second determination processing is acquired from one of the heater, the container, and the transporter other than the element.

The present invention in its second aspect provides an inhalation device controller comprising a holder configured to hold an atomizer including a heater for atomizing an aerosol source, and, a processor configured to execute, upon detecting an atomization request, first determination processing of determining presence/absence of the aerosol source in the atomizer using a first algorithm, and execute, only if aerosol presence is determined by the first determination processing, a second determination processing of determining a remaining amount of the aerosol source in the atomizer using a second algorithm different from the first algorithm.

The present invention in its third aspect provides an inhalation device controller comprising a holder configured to hold an atomizer including a heater for atomizing an aerosol source, and a processor configured to execute first determination processing of determining one of presence/absence and a remaining amount of the aerosol source in the atomizer held by the holder using a first algorithm, and second determination processing of determining one of the presence/absence and the remaining amount using a second algorithm different from the first algorithm, wherein the atomizer further comprises a container configured to hold the aerosol source, and a transporter configured to transport the aerosol source in the container to a position at which the aerosol source can be heated by the heater, a variable necessary for executing the first determination processing is acquired from one element of the heater, the container, and the transporter, and a variable necessary for executing the second determination processing is acquired from one of the heater, the container, and the transporter other than the element.

Further features of the present invention will become apparent from the following description of exemplary embodiments (with reference to the attached drawings).

BRIEF DESCRIPTION OF THE DRAWINGS

FIG. 4 is a view showing the first operation example of the inhalation device including processing of determining the presence/absence and the remaining amount of an aerosol source in an atomizer;

FIG. 7 is a view showing the fourth operation example of the inhalation device including processing of determining the remaining amount of the aerosol source in the atomizer;

FIG. 8 is a view showing the fifth operation example of the inhalation device including processing of determining the presence/absence of the aerosol source in the atomizer;

DESCRIPTION OF THE EMBODIMENTS

Figure 1:
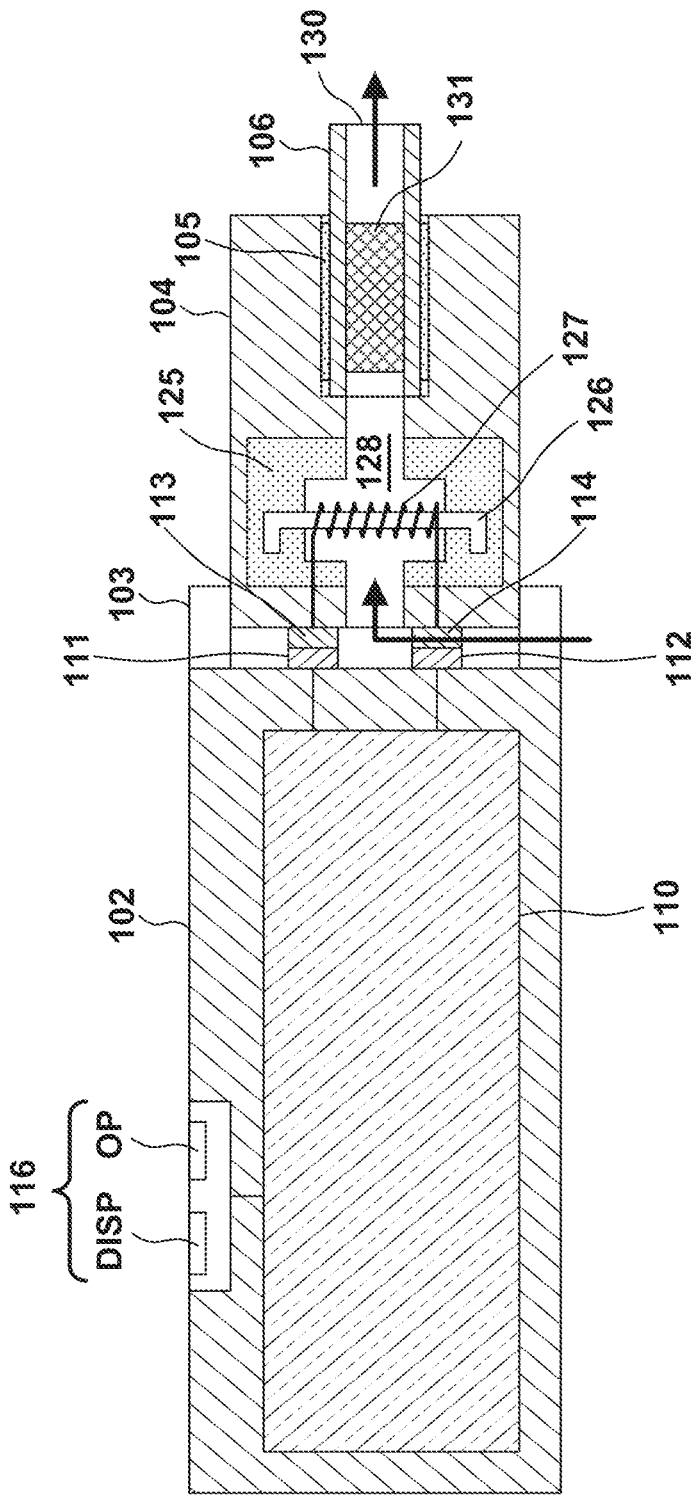
FIG. 1 is a view schematically showing the arrangement of an inhalation device according to an embodiment.

Hereinafter, embodiments will be described in detail with reference to the attached drawings. Note that the following embodiments are not intended to limit the scope of the claimed invention, and limitation is not made an invention that requires all combinations of features described in the embodiments. Two or more of the multiple features described in the embodiments may be combined as appropriate. Furthermore, the same reference numerals are given to the same or similar configurations, and redundant description thereof is omitted.

FIG. 1 schematically shows the arrangement of an inhalation device 100 according to an embodiment. The inhalation device can be configured to provide a gas containing an aerosol or a gas containing an aerosol and a flavor substance to a user via a mouthpiece 130 in accordance with an inhalation operation of the user. The inhalation device 100 can include a controller 102 and an atomizer 104. The inhalation device 100 can include a holder 103 that holds the atomizer 104 in a detachable state. The controller 102 can be understood as an inhalation device controller. The atomizer 104 can be configured to atomize an aerosol source. The aerosol source can be, for example, a liquid such as a polyhydric alcohol such as glycerin or propylene glycerol. Alternatively, the aerosol source may contain a drug. The aerosol source may be a liquid, a solid, or a mixture of a liquid and a solid. A vapor source such as water may be used in place of the aerosol source.

The inhalation device 100 may further include a capsule 106 including a flavor source 131, and the atomizer 104 can include a capsule holder 105 that holds the capsule 106 in a detachable state. The capsule holder 105 may be included not in the atomizer 104 but in the controller 102. The flavor source 131 can be, for example, a molded body formed by molding a tobacco material. Alternatively, the flavor source 131 may be formed by a plant (for example, mint, herb, Chinese herb, coffee bean, and the like) other than tobacco. A flavor such as menthol may be added to the flavor source. The flavor source 131 may be added to the aerosol source.

The controller 102 can include an electric component 110. The electric component 110 can include a user interface 116. Alternatively, it may be understood that the controller 102 includes the electric component 110 and the user interface 116. The user interface 116 can include, for example, a display unit DISP (for example, a light emitting element such as an LED and/or an image display device such as an LCD) and/or an operation unit OP (for example, a switch such as a button switch).

The holder 103 of the controller 102 can include a first electrical contact 111 and a second electrical contact 112. In a state in which the atomizer 104 is held by the holder 103, the first electrical contact 111 of the holder 103 can contact a third electrical contact 113 of the atomizer 104, and the second electrical contact 112 of the holder 103 can contact a fourth electrical contact 114 of the atomizer 104. The controller 102 can supply power to the atomizer 104 via the first electrical contact 111 and the second electrical contact 112.

The atomizer 104 can include the third electrical contact 113 and the fourth electrical contact 114 described above. In addition, the atomizer 104 can include a heater 127 that heats the aerosol source, a container 125 that holds the aerosol source, and a transporter (wick) 126 that transports the aerosol source held by the container 125 to a heating area by the heater 127. At least a part of the heating area can be arranged in a channel 128 provided in the atomizer 104. The first electrical contact 111, the third electrical contact 113, the heater 127, the fourth electrical contact 114, and the second electrical contact 112 form a current path configured to flow a current to the heater 127. The transporter 126 can be made of, for example, a fiber material or a porous material.

As described above, the atomizer 104 can include the capsule holder 105 that detachably holds the capsule 106. In an example, the capsule holder 105 can hold the capsule 106 such that a part of the capsule 106 is stored in the capsule holder 105 or the atomizer 104, and the other part is exposed. The user can inhale a gas containing an aerosol by holding the mouthpiece 130 in the mouth. When the mouthpiece 130 is provided in the detachable capsule 106, the inhalation device 100 can be kept clean.

When the user holds the mouthpiece 130 in the mouth and performs an inhalation operation, air flows into the channel 128 of the atomizer 104 via an opening (not shown), and an aerosol generated by heating the aerosol source by the heater 127 is transported to the mouthpiece 130, as indicated by arrows. In the arrangement in which the flavor source 131 is arranged, a flavor substance generated from the flavor source 131 is added to the aerosol, transported to the mouthpiece 130, and inhaled into the mouth of the user.

Figure 2:
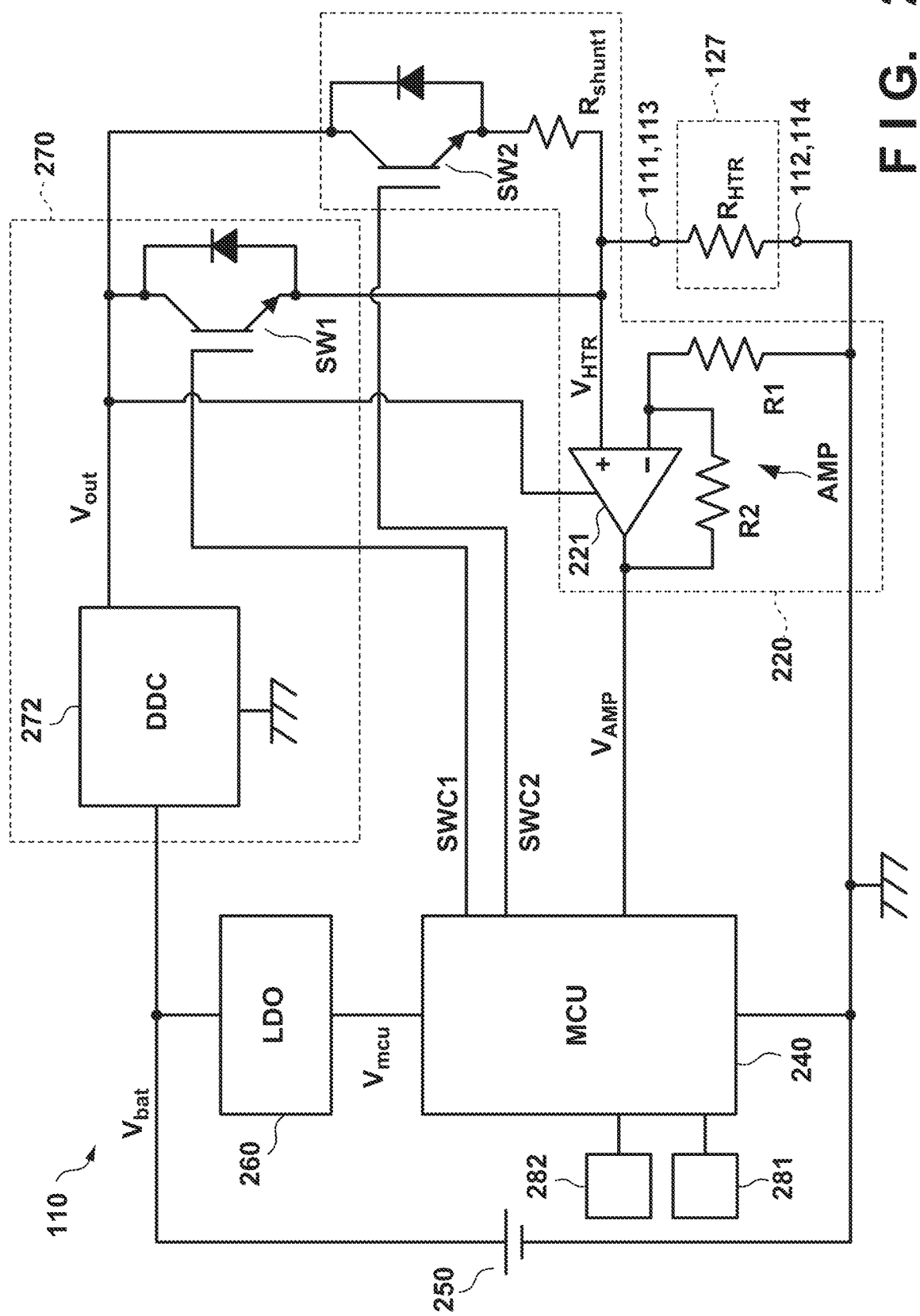
FIG. 2 is a view showing an example of the arrangement of an electric component.

FIG. 2 shows the first arrangement example of the electric component 110. The electric component 110 can include a power supply (battery) 250, a power supply unit 270 that supplies power to (the heater 127 of) the atomizer 104, a detection circuit 220 configured to detect the resistance value of the heater 127, and a processor 240 that generates a control signal in accordance with a smoothed signal generated by smoothing information obtained using the detection circuit 220. The heater 127 has a resistance value $R_{HTR}$ that changes depending on the temperature of the heater 127.

The power supply unit 270 can include a switch SW1 arranged in a current path configured to supply a current to the heater 127. Opening/closing (off/on) of the switch SW1 can be controlled by a control signal SWC1 generated by the processor 240 in accordance with the smoothed signal. The power supply unit 270 can include, for example, a voltage converter 272 that converts a power supply voltage $V_{bat}$ supplied from the power supply 250 into a heater driving voltage $V_{out}$. The switch SW1 can be arranged to form a current path configured to supply a current to the heater 127 between the ground line and the supply line of the heater driving voltage $V_{out}$. The switch SW1 can be arranged, for example, between the heater 127 and the supply line of the heater driving voltage $V_{out}$.

The detection circuit 220 can include a shunt resistor $R_{shunt1}$ and a switch SW2, which are arranged, in series with the heater 127, between the ground line and the supply line of the heater driving voltage $V_{out}$. Also, the detection circuit 220 can include an amplifier AMP that detects a voltage $V_{HTR}$ applied to the heater 127. Here, the resistance value of the shunt resistor $R_{shunt1}$ will be expressed as $R_{shunt1}$, like the reference symbol. The amplifier AMP includes, for example, a differential amplifier 221 including a noninverting input terminal, an inverting input terminal, and an output terminal, a resistive element R1 that connects the inverting input terminal and the ground line, and a resistive element R2 that connects the inverting input terminal and the output terminal, and the voltage $V_{HTR}$ can be input to the noninverting input terminal. In this arrangement example, if the resistance value of the resistive element R1 is expressed as R1, and the resistance value of the resistive element R2 is expressed as R2, an amplification factor A of the amplifier AMP is (1+R2/R1). The switch SW2 can be controlled by a control signal SWC2 generated by the processor 240.

To detect the resistance value $R_{HTR}$ of the heater 127, the switch SW1 is turned off, and the switch SW2 is turned on. At this time, letting $I_{HTR}$ be a current flowing to $R_{HTR}$, $R_{HTR}$ is given by $$R_{HTR}=V_{HTR}/I_{HTR}=V_{HTR} \cdot (R_{HTR}+R_{shunt1})/V_{out} \quad (1)$$

When equation (1) is deformed, we obtain equation (2) that gives $R_{HTR}$.

$$R_{HTR}=R_{shunt1} \cdot V_{HTR}/(V_{out}-V_{HTR}) \quad (2)$$

An output voltage $V_{AMP}$ of the amplifier AMP of the detection circuit 220 is given by $$V_{AMP}=A \cdot V_{HTR}. \quad (3)$$

When equation (3) is deformed, we obtain equation (4) that gives $V_{HTR}$.

$$V_{HTR}=V_{AMP}/A \quad (4)$$

Hence, the resistance value $R_{HTR}$ of the heater 127 can be obtained in accordance with equations (2) and (4).

The processor 240 can include an input terminal to which the output voltage $V_{AMP}$ of the amplifier AMP of the detection circuit 220 is input, and an A/D converter that converts an analog signal that is a voltage input to the input terminal into a digital signal. The processor 240 can generate a control signal in accordance with a smoothed signal generated by smoothing information (here, $V_{AMP}$) obtained using the detection circuit 220. The control signal can be, for example, the control signal SWC1 but can include another control signal (for example, a control signal that controls the display unit DISP).

The processor 240 can be formed by, for example, an MCU (Micro Controller Unit). However, the processor 240 may be formed by an MCU and an analog circuit. To the processor 240, a voltage $V_{mcu}$ can be supplied from a voltage conversion circuit 260 such as an LDO (Low DropOut) that converts the power supply voltage $V_{bat}$ into the voltage $V_{mcu}$ for the processor 240. The processor 240 can calculate the resistance value $R_{HTR}$ of the heater 127 in accordance with equations (2) and (4) based on $R_{shunt1}$ that is a known value, $V_{out}$, and $V_{AMP}$ that is supplied from the amplifier AMP.

The processor 240 can calculate the temperature of the heater 127 in accordance with equation (5) based on the resistance value $R_{HTR}$ of the heater 127.

$$T=T_{ref}+(1/\alpha) \cdot (R_{HTR}-R_{ref}) \cdot (1/R_{ref}) \cdot 10^6 \quad (5)$$

where $T_{ref}$ is the reference temperature, $R_{ref}$ is the reference resistance value, and this is the resistance value $R_{HTR}$ of the heater 127 at the reference temperature. α is the temperature coefficient [ppm/° C.] of the heater 127. Note that the reference temperature can be an arbitrary temperature, and the temperature of the heater 127 obtained when acquiring the reference resistance value is the resistance temperature. As the temperature of the heater 127 obtained when acquiring the reference resistance value, the temperature of an arbitrary portion in the inhalation device 100 (for example, a temperature detected by a temperature sensor 282 to be described later) can be used.

Based on the temperature of the heater 127, the processor 240 can generate the control signal SWC1 used to control the switch SW1 such that the temperature of the heater 127 matches a target temperature. The processor 240 receives a signal from the operation unit OP of the user interface 116, and provides a signal for display control to the display unit DISP of the user interface 116. The electric component 110 can include a puff sensor (for example, a pressure sensor) 281 that detects the puff operation of the user, and the temperature sensor 282 that detects the temperature of a predetermined portion of the electric component 110. The temperature sensor 282 may be incorporated in the puff sensor 281, the power supply 250, or the processor 240.

Figure 3A:
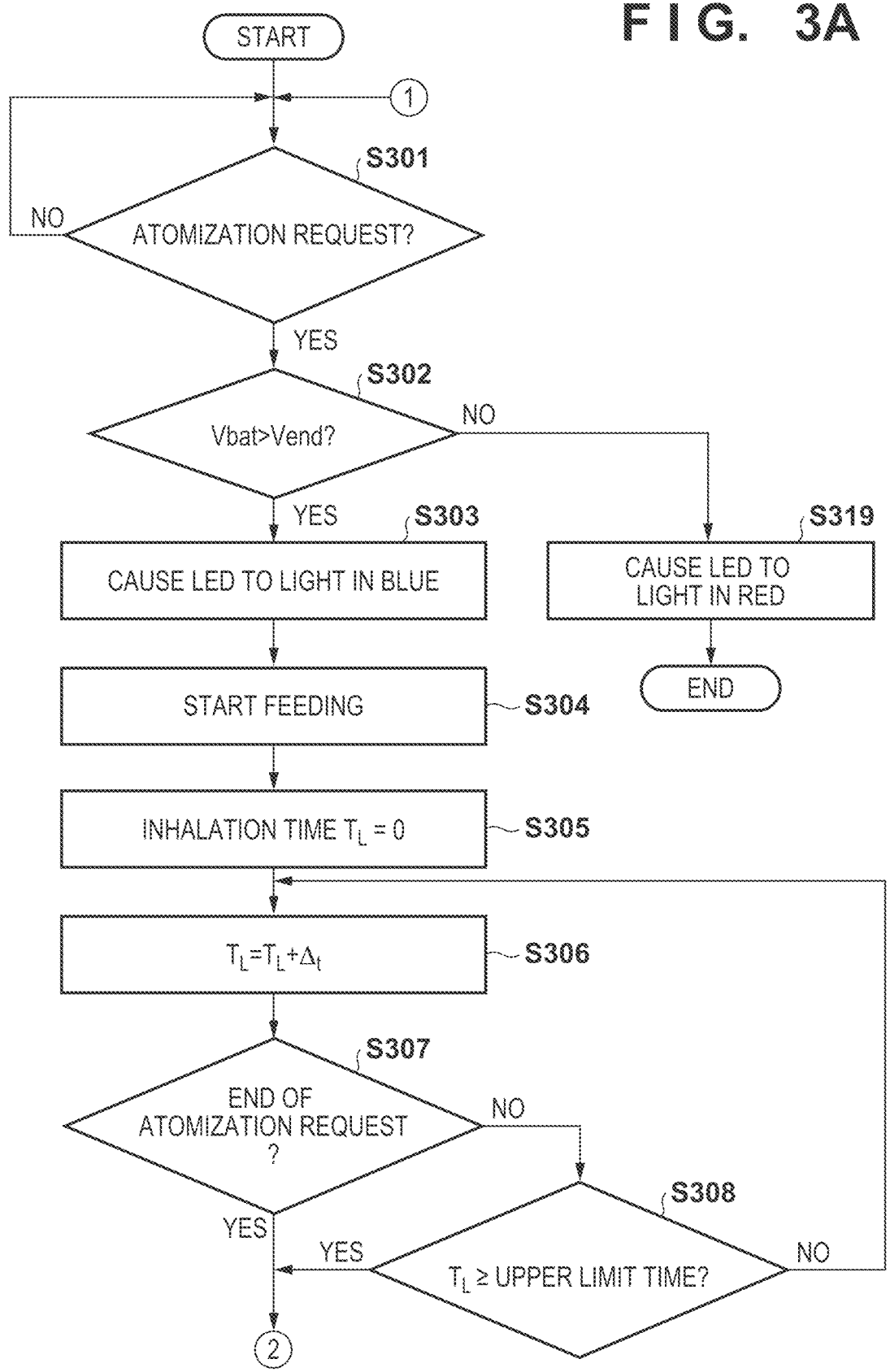
FIGS. 3A and 3B are flowcharts showing the operation of the inhalation device according to an embodiment.
Figure 3B:
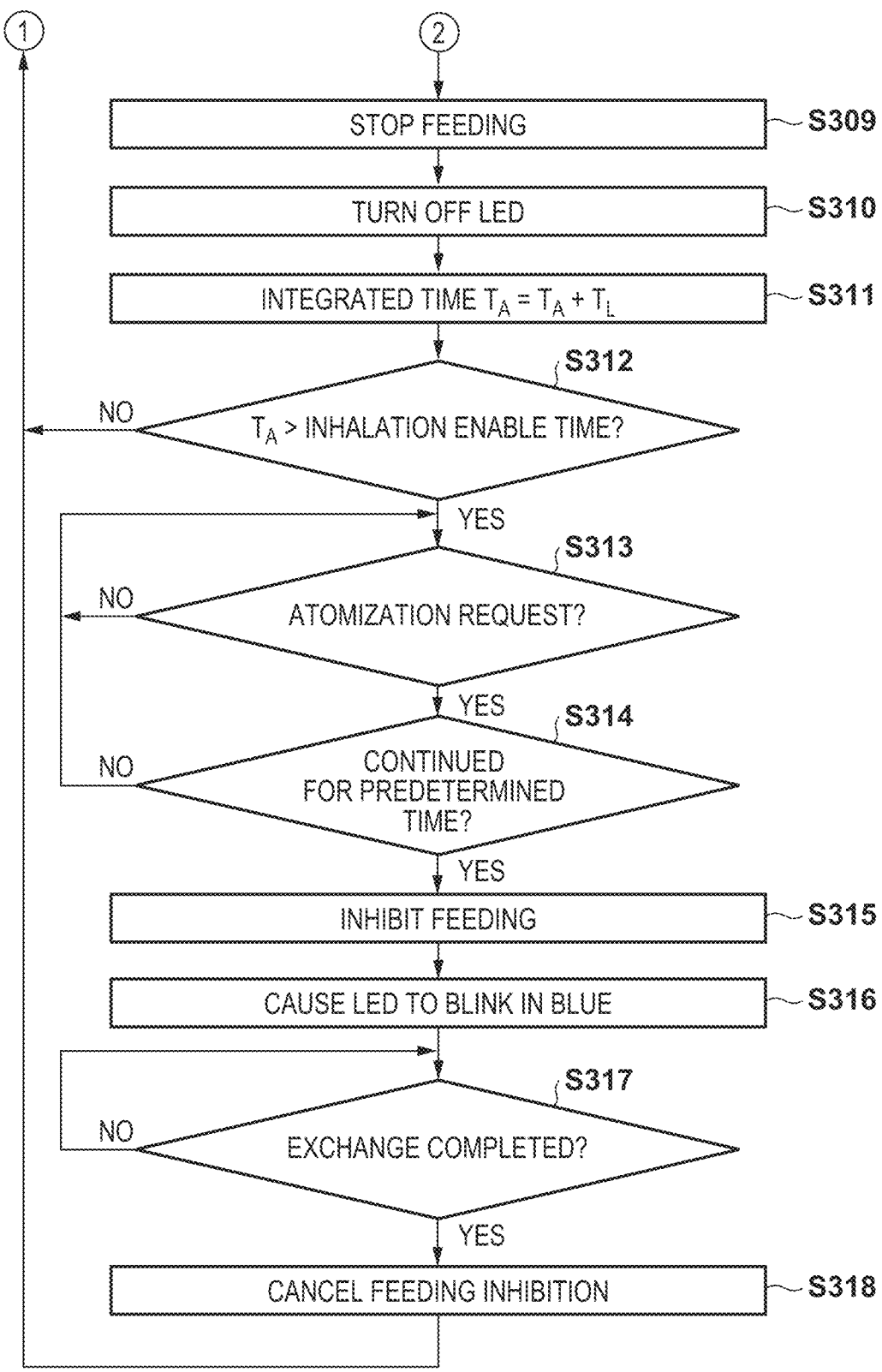

FIGS. 3A and 3B show the operation of the inhalation device 100. This operation is controlled by the processor 240. The processor 240 includes a memory that stores a program, and a CPU that operates in accordance with the program. For example, a program corresponding to each flowchart shown in the accompanying drawings is stored in the memory, and the program is executed by the CPU.

In step S301, the processor 240 waits for reception of an atomization request, and upon receiving an atomization request, executes step S302. The atomization request is a request for operating the atomizer 104, more specifically, controlling the heater 127 within a target temperature range to generate an aerosol from the aerosol source. The atomization request can be an operation of detecting, by the puff sensor 281, that the user has performed the inhalation operation (puff operation) via the mouthpiece 130, and notifying, by the puff sensor 281, the processor 240 of the detection. Alternatively, the atomization request can be an operation of notifying, by the operation unit OP, the processor 240 that the user has operated the operation unit OP.

In step S302, the processor 240 acquires the power supply voltage $V_{bat}$ from a power supply management circuit (not shown), and determines whether the power supply voltage $V_{bat}$ is higher than a discharge end voltage $V_{end}$ (for example, 3.2 V). That the power supply voltage $V_{bat}$ is equal to or lower than the discharge end voltage $V_{end}$ means that the remaining dischargeable amount of the power supply 250 is not sufficient. Hence, if the power supply voltage $V_{bat}$ is equal to or lower than the discharge end voltage $V_{end}$, in step S319, the processor 240 makes a notification to promote charge of the power supply 250 using the display unit DISP of the user interface 116. If the display unit DISP includes an LED, this notification can be causing the LED to light in red. If the power supply voltage $V_{bat}$ is higher than the discharge end voltage $V_{end}$, in step S303, using the display unit DISP of the user interface 116, the processor 240 can make a notification representing that a normal operation is possible. If the display unit DISP includes an LED, this notification can be causing the LED to light in blue.

Next to step S303, in step S304, the processor 240 starts feed control for the heater 127. Feed control for the heater 127 includes temperature control of controlling the heater 127 within a target temperature range. Temperature control can include feedback control of detecting the temperature of the heater 127 by detecting the resistance value $R_{HTR}$ of the heater 127 and controlling opening/closing of the switch SW1 by the control signal SWC1 based on the detection result.

Next, in step S305, the processor 240 resets an inhalation time TL to 0. After that, in step S306, the processor 240 adds Δt to the inhalation time TL. At corresponds to the time interval between execution of step S306 and the next execution of step S306.

Next, in step S307, the processor 240 determines whether the atomization request has ended. If the atomization request has ended, in step S309, the processor 240 stops feed control for the heater 127. On the other hand, if the atomization request has not ended, in step S308, the processor 240 determines whether the inhalation time TL has reached an upper limit time. If the inhalation time TL has not reached the upper limit time, the process returns to step S306. As an example, the upper limit time may be 2.0 to 2.5 sec.

Next to step S309, in step S310, the processor 240 turns off the LED that is lighting in blue. Next, in step S311, the processor 240 updates an integrated time $T_A$. More specifically, in step S311, the inhalation time TL is added to the integrated time $T_A$ at the current point of time. The integrated time $T_A$ can be an integrated time when the capsule 106 was used for inhalation, in other words, an integrated time when the aerosol was inhaled via the flavor source 131 of the capsule 106.

In step S312, the processor 240 determines whether the integrated time $T_A$ is not more than an inhalation enable time (for example, 120 sec). If the integrated time $T_A$ is not more than the inhalation enable time, this means that the capsule 106 can still provide the flavor substance. In this case, the process returns to step S301. If the integrated time $T_A$ is more than the inhalation enable time, in step S313, the processor 240 waits for generation of the atomization request. If the atomization request is generated, in step S314, the processor 240 waits for continuation of the atomization request for a predetermined time. After that, in step S315, the processor 240 inhibits feed control for the heater 127. Note that step S314 may be omitted.

Next, in step S316, using the display unit DISP of the user interface 116, the processor 240 can make a notification to promote exchange of the capsule 106. If the display unit DISP includes an LED, this notification can be causing the LED to blink in blue (repeat on/off). Hence, the user can exchange the capsule 106. In an example, one atomizer 104 and a plurality of (for example, five) capsules 106 can be sold as one set. In this example, after one atomizer 104 and all capsules 106 in one set are consumed, the atomizer 104 and the last capsule 106 in the consumed set can be exchanged with an atomizer 104 and a capsule 106 of a new set.

In step S317, the processor 240 waits for completion of the exchange of the capsule 106 (or the capsule 106 and the atomizer 104). In step S318, the processor 240 cancels inhibition of feed control for the heater 127 and returns to step S301.

The operation of the inhalation device 100 including processing of determining the presence/absence or the remaining amount of the aerosol source in the atomizer 104 will be described below. Note that in this specification, the remaining amount of the aerosol source may be a value representing the absolute value of the aerosol source held in (the container 125 of) the atomizer 104, or may be a value represented by the ratio of the remaining amount of the aerosol source to the full amount of the aerosol source that can be held in (the container 125 of) the atomizer 104. In addition, the presence/absence of the aerosol source is represented by a binary value representing whether the aerosol source exists in (the container 125 of) the atomizer 104. Here, aerosol source absence indicates a state in which the remaining amount of the aerosol source is 0 or almost 0, and this state is also expressed as the aerosol source is "exhausted". In addition, aerosol source presence indicates a state in which the remaining amount of the aerosol source is so sufficient not to impede a normal inhalation operation.

In the embodiment, the processor 240 is configured to execute first determination processing of determining, by a first algorithm, the presence/absence or the remaining amount of the aerosol source in the atomizer 104 held by the holder 103, and second determination processing of determining the presence/absence or the remaining amount of the aerosol source by a second algorithm different from the first algorithm.

First Operation Example

FIG. 4 shows the first operation example of the inhalation device 100 including processing of determining the presence/absence or the remaining amount of the aerosol source in the atomizer 104. In the first operation example, first determination processing is processing of determining the remaining amount of the aerosol source by the first algorithm, and second determination processing is processing of determining the presence/absence of the aerosol source by the second algorithm. For example, the first algorithm can be an algorithm selected from algorithms B1 to B6 to be described later, and the second algorithm can be an algorithm selected from algorithms A1 to A8 to be described later.

In step S401, the processor 240 determines whether an event for updating the remaining amount of the aerosol source is detected. The event for updating the remaining amount of the aerosol source can be pressing of a power supply button or a remaining amount display button (neither are shown), an atomization request, or the like. If an event for updating the remaining amount of the aerosol source is detected, the process advances to step S402. If the event is not detected, the process advances to step S406.

In step S402, the processor 240 acquires a first parameter that is a variable necessary for executing the first determination processing. The first parameter can be the resistance value $R_{HTR}$ or temperature of the heater 127 according to the first algorithm employed in the first determination processing. In step S403, the processor 240 executes the first determination processing by the first algorithm using the first parameter acquired in step S402, thereby acquiring the remaining amount of the aerosol source. The remaining amount acquired by the first determination processing is defined as a first remaining amount. In step S404, the processor 240 updates the remaining amount stored in the memory by the first remaining amount. In step S405, the processor 240 causes the display unit DISP of the user interface 116 to display the remaining amount after updating. If the display unit DISP includes a plurality of LEDs, the remaining amount can be displayed by graph display by the plurality of LEDs.

In step S406, the processor 240 determines whether an event for updating the presence/absence of the aerosol source is detected. The event for updating the presence/absence of the aerosol source can be, for example, an atomization request. If an event for updating the presence/absence of the aerosol source is detected, the process advances to step S407. If the event is not detected, this operation is ended.

Figure 9A:
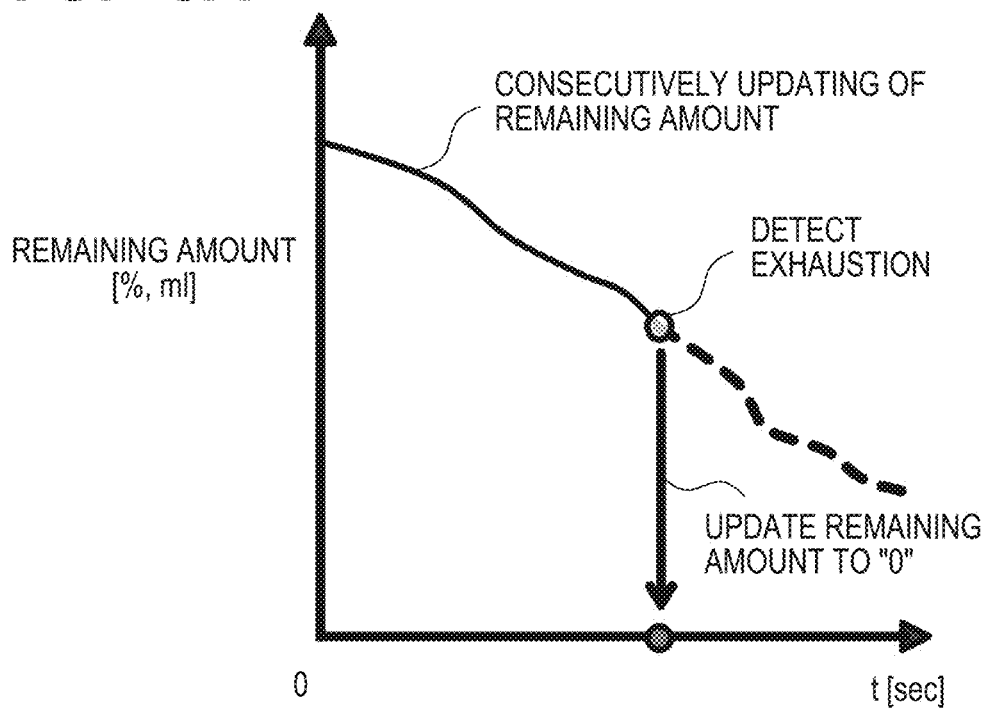
FIG. 9A is a view showing the concept of updating of the remaining amount of the aerosol source and detection of exhaustion according to the first operation example.

In step S407, the processor 240 acquires a second parameter that is a variable necessary for executing the second determination processing. The second parameter can be the resistance value $R_{HTR}$ or temperature of the heater 127 according to the second algorithm employed in the second determination processing. In step S408, the processor 240 executes the second determination processing by the second algorithm using the second parameter acquired in step S407. In step S409, the processor 240 determines whether the result of the second determination processing represents aerosol source absence (that is, exhaustion). Upon determining aerosol source presence, this processing is ended. On the other hand, upon determining aerosol source absence, the process advances to step S410. Even if it is determined by the first determination processing in step S403 that the remaining amount is larger than 0, aerosol source absence (that is, exhaustion) may be determined in step S409. In this case, the processor 240 gives priority to the determination of aerosol source absence in step S409, and outputs a final determination result of aerosol source absence, as shown in FIG. 9A. In step S410, according to the final determination result of aerosol source absence, the processor 240 inhibits feeding to the heater 127, thereby inhibiting generation of an aerosol.

Next, in step S411, the processor 240 updates the remaining amount stored in the memory to 0. In step S412, the processor 240 makes a notification representing the remaining amount (that is, a remaining amount of 0) after updating using the display unit DISP of the user interface 116. This notification can be causing an LED to blink in red to emphasize the notification of the exhaustion of the aerosol source. If the user interface 116 includes a vibration unit, the processor 240 may cause the vibration unit to generate a vibration to promote exchange of the atomizer.

As described above, in this operation example, it is possible to accurately determine the presence/absence and the remaining amount of the aerosol source by the combination of the first determination processing and the second determination processing of different determination algorithms. Also, according to this operation example, even if it is determined by the first determination processing that the remaining amount is larger than 0, if aerosol source absence is determined by the second determination processing, priority is given to the determination result of aerosol source absence, and generation of an aerosol is inhibited. It is therefore possible to reliably prevent a situation in which heater heating is continued regardless of the exhaustion of the aerosol source. In addition, generation of an undesirable flavor can more reliably be suppressed.

Second Operation Example

Figure 5:
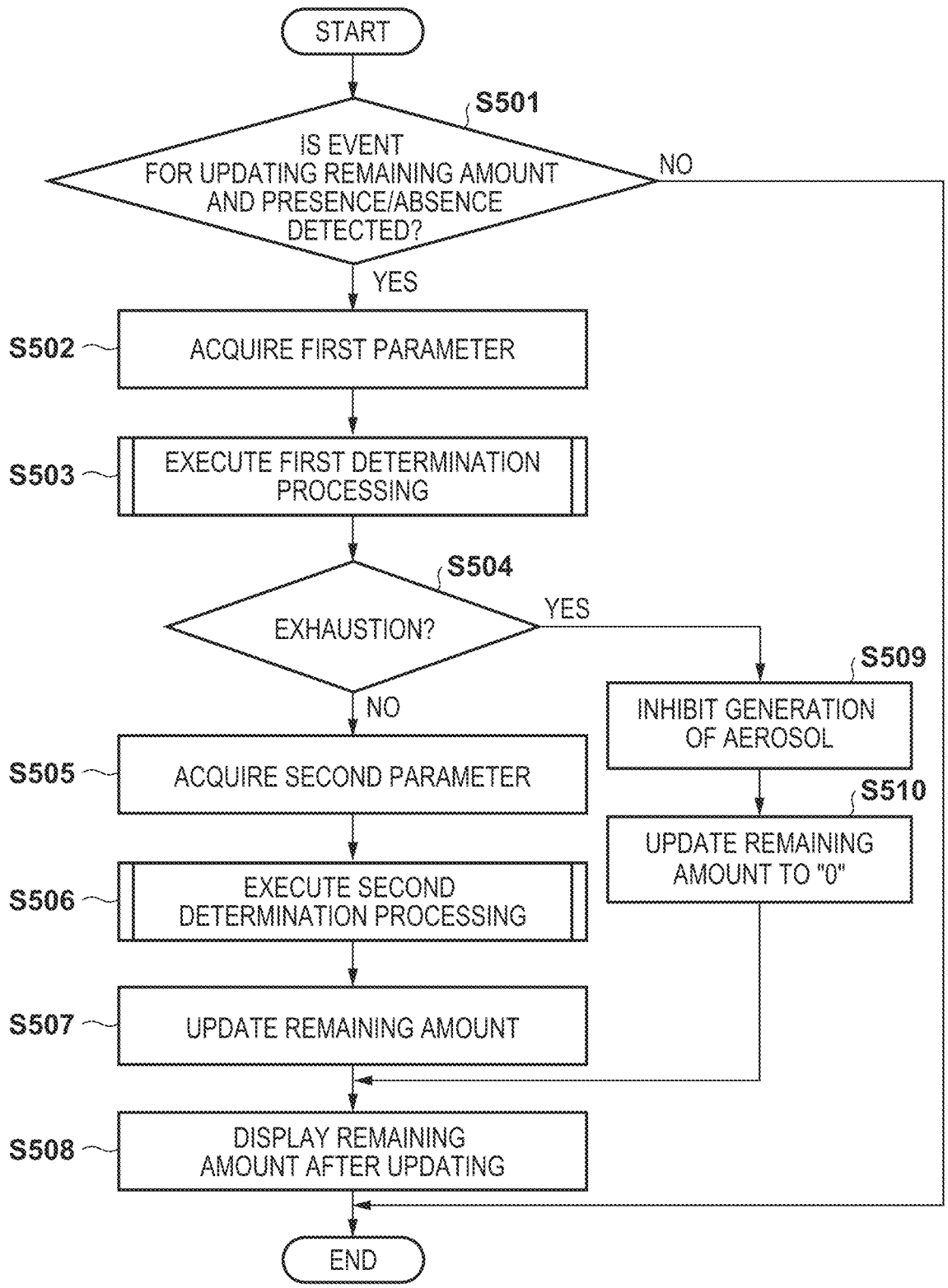
FIG. 5 is a view showing the second operation example of the inhalation device including processing of determining the presence/absence and the remaining amount of the aerosol source in the atomizer.

FIG. 5 shows the second operation example of the inhalation device 100 including processing of determining the presence/absence or the remaining amount of the aerosol source in the atomizer 104. In the second operation example, first determination processing is processing of determining the presence/absence of the aerosol source by the first algorithm, and second determination processing is processing of determining the remaining amount of the aerosol source by the second algorithm. For example, the first algorithm can be an algorithm selected from algorithms A1 to A8 to be described later, and the second algorithm can be an algorithm selected from algorithms B1 to B6 to be described later.

In step S501, the processor 240 determines whether an event for updating the remaining amount and the presence/absence of the aerosol source is detected. The event for updating the remaining amount and the presence/absence of the aerosol source can be pressing of a power supply button or a remaining amount display button (neither are shown), an atomization request, or the like. If an event for updating the remaining amount and the presence/absence of the aerosol source is detected, the process advances to step S502. If the event is not detected, this operation is ended.

In step S502, the processor 240 acquires a first parameter that is a variable necessary for executing the first determination processing. In step S503, the processor 240 executes the first determination processing by the first algorithm using the first parameter acquired in step S502. In step S504, the processor 240 determines whether the result of the first determination processing represents aerosol source absence (that is, exhaustion). Upon determining aerosol source presence, the process advances to step S505, and the processor 240 acquires a second parameter that is a variable necessary for executing the second determination processing. In step S506, the processor 240 executes the second determination processing by the second algorithm using the second parameter acquired in step S505. In step S507, the processor 240 updates the remaining amount stored in the memory by the remaining amount determined by the second determination processing in step S506. After that, in step S508, the processor 240 causes the display unit DISP of the user interface 116 to display the remaining amount after updating.

On the other hand, upon determining aerosol source absence (that is, exhaustion) in step S504, the process advances to step S509, and the processor 240 inhibits feeding to the heater 127, thereby inhibiting generation of an aerosol. Next, in step S510, the processor 240 updates the remaining amount stored in the memory to 0. After that, in step S508, the processor 240 makes a notification representing the remaining amount (that is, a remaining amount of 0) after updating using the display unit DISP of the user interface 116. The notification in this case can be causing an LED to blink in red to emphasize the notification of the exhaustion of the aerosol source. If the user interface 116 includes a vibration unit, the processor 240 may cause the vibration unit to generate a vibration to promote exchange of the atomizer.

As described above, in this operation example, if aerosol source absence is determined by the first determination processing (if YES in step S504), the second determination processing (remaining amount determination) is not executed. Only when aerosol source presence is determined by the first determination processing (if NO in step S504), the second determination processing (remaining amount determination) is executed. This can prevent aerosol source remaining amount determination from being executed even if it is determined that the aerosol source is exhausted. It is therefore possible to reduce power consumption and load of the processor 240.

Third Operation Example

Figure 6:
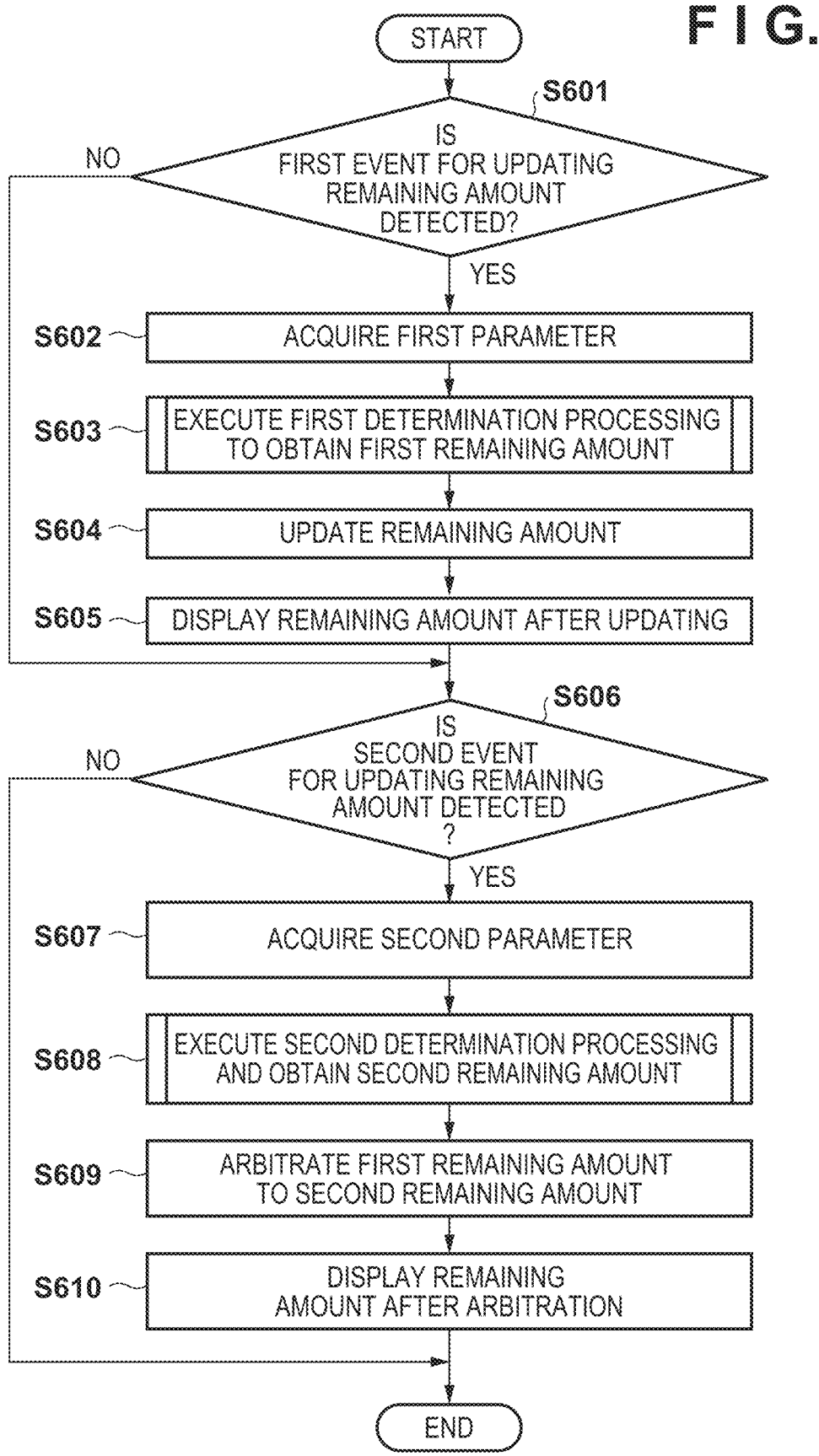
FIG. 6 is a view showing the third operation example of the inhalation device including processing of determining the remaining amount of the aerosol source in the atomizer.

FIG. 6 shows the third operation example of the inhalation device 100 including processing of determining the presence/absence of the aerosol source in the atomizer 104. In the third operation example, first determination processing is processing of determining the remaining amount of the aerosol source by the first algorithm, and second determination processing is processing of determining the remaining amount of the aerosol source by the second algorithm. For example, the first algorithm can be an algorithm selected from algorithms B1 to B6 to be described later, and the second algorithm can be an algorithm selected from algorithms B1 to B6 other than the first algorithm.

In step S601, the processor 240 determines whether a first event for updating the remaining amount of the aerosol source is detected. The first event can be pressing of a power supply button or a remaining amount display button (neither are shown), an atomization request, or the like. If the first event is detected, the process advances to step S602. If the first event is not detected, the process advances to step S606.

In step S602, the processor 240 acquires a first parameter that is a variable necessary for executing the first determination processing. In step S603, the processor 240 executes the first determination processing by the first algorithm using the first parameter acquired in step S602, thereby acquiring the remaining amount of the aerosol source. In step S604, the processor 240 updates the remaining amount stored in the memory by the remaining amount acquired in step S603. In step S605, the processor 240 causes the display unit DISP of the user interface 116 to display the remaining amount (second amount) after updating. If the display unit DISP includes a plurality of LEDs, the remaining amount can be displayed by graph display by the plurality of LEDs.

In step S606, the processor 240 determines whether a second event for updating the remaining amount of the aerosol source is detected. The second event can be, for example, an atomization request. If the second event is detected, the process advances to step S607. If the second event is not detected, this operation is ended.

In step S607, the processor 240 acquires a second parameter that is a variable necessary for executing the second determination processing. In step S608, the processor 240 executes the second determination processing by the second algorithm using the second parameter acquired in step S607, thereby acquiring the remaining amount of the aerosol source. The remaining amount acquired by the second determination processing is defined as a second remaining amount.

In step S609, the processor 240 acquires the remaining amount (first amount) of the aerosol source based on the first remaining amount obtained in step S603 and the second remaining amount obtained in step S608. Here, the processor 240 arbitrates the first remaining amount obtained in step S603 and the second remaining amount obtained in step S608, thereby acquiring the remaining amount (first amount) of the aerosol source. The arbitration may be performed by calculating a simple average or a weighted average of the first remaining amount obtained in step S603 and the second remaining amount obtained in step S608.

In step S610, the processor 240 updates the remaining amount stored in the memory by the remaining amount after arbitration (updates the second amount by the first amount) and causes the display unit DISP of the user interface 116 to display the remaining amount (the first amount in place of the second amount) after updating.

Figure 9B:
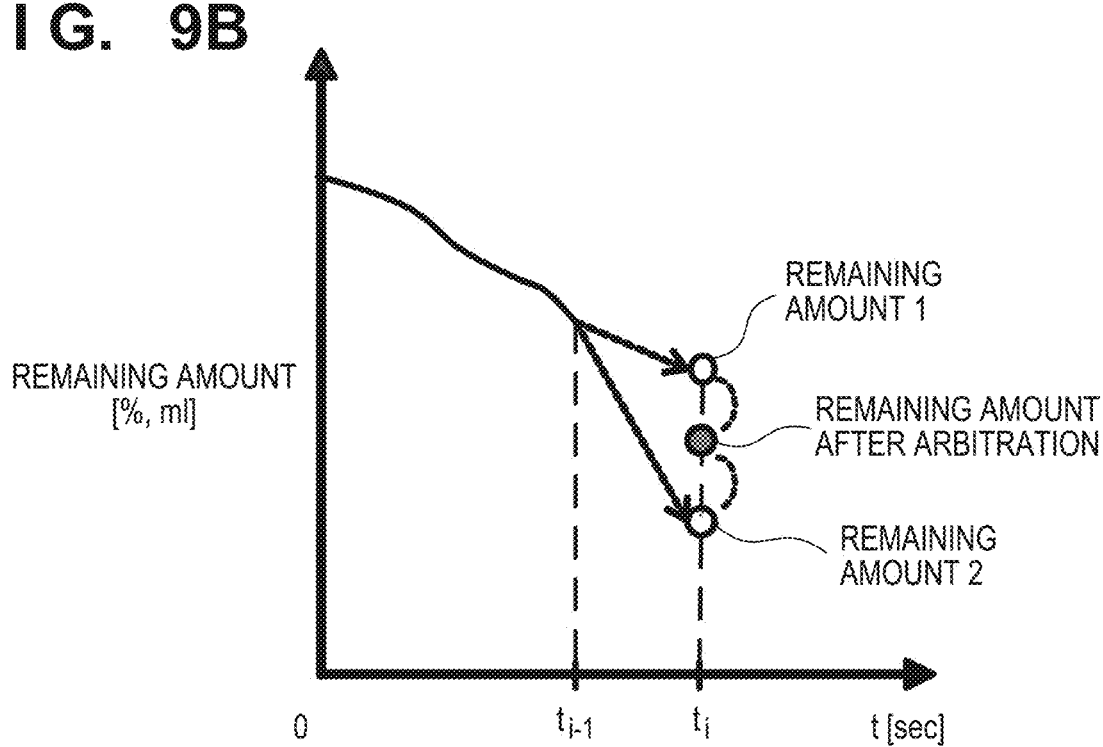
FIG. 9B is a view showing the concept of updating of the remaining amount of the aerosol source according to the third operation example.

As described above, in this operation example, since the remaining amount of the aerosol source is determined by each of the first determination processing and the second determination processing using different determination algorithms, and the remaining amounts are arbitrated, as shown in FIG. 9B, the remaining amount can more accurately be determined. Note that the remaining amount displayed in step S605 is an intermediate value (temporary value) for the remaining amount displayed in step S610. When such a temporary value is displayed, it is possible to quickly provide the latest remaining amount to the user. However, in some cases, the remaining amount displayed in step S610 is larger than the remaining amount displayed in step S605. To suppress the behavior that the displayed remaining amount becomes large, remaining amount display in step S605 may be omitted. If remaining amount display in step S605 is omitted, the displayed remaining amount is not updated until completion of the arbitration in step S609. This allows the user to know a correct remaining amount.

Fourth Operation Example

FIG. 7 shows the fourth operation example of the inhalation device 100 including processing of determining the presence/absence of the aerosol source in the atomizer 104. The fourth operation example is a modification of the third operation example. In the fourth operation example, first determination processing is processing of determining the remaining amount of the aerosol source by the first algorithm, and second determination processing is processing of determining the remaining amount of the aerosol source by the second algorithm, as in the third operation example.

In step S701, the processor 240 determines whether a first event for updating the remaining amount of the aerosol source is detected. The first event can be pressing of a power supply button or a remaining amount display button (neither are shown), an atomization request, or the like. If the first event is detected, the process advances to step S702. If the first event is not detected, this processing is ended.

In step S702, the processor 240 acquires a first parameter that is a variable necessary for executing the first determination processing and a second parameter that is a variable necessary for executing the second determination processing. In step S703, the processor 240 executes the first determination processing by the first algorithm using the first parameter acquired in step S702, thereby acquiring the remaining amount of the aerosol source as the first remaining amount, and also executes the second determination processing by the second algorithm using the second parameter acquired in step S702, thereby acquiring the remaining amount of the aerosol source as the second remaining amount.

In step S704, the processor 240 updates the first remaining amount and the second remaining amount stored in the memory by the first remaining amount and the second remaining amount acquired in step S703. In step S705, the processor 240 causes the display unit DISP of the user interface 116 to display the first remaining amount or the second remaining amount as a temporary value. If the display unit DISP includes a plurality of LEDs, the remaining amount can be displayed by graph display by the plurality of LEDs.

In step S706, the processor 240 arbitrates the first remaining amount and the second remaining amount. The arbitration may be performed by calculating a simple average or a weighted average of the first remaining amount and the second remaining amount. Next, in step S707, the processor 240 causes the display unit DISP of the user interface 116 to display the remaining amount after arbitration.

Fifth Operation Example

FIG. 8 shows the fifth operation example of the inhalation device 100 including processing of determining the presence/absence of the aerosol source in the atomizer 104. In the fifth operation example, first determination processing is processing of determining the presence/absence of the aerosol source by the first algorithm, and second determination processing is processing of determining the presence/absence of the aerosol source by the second algorithm. For example, the first algorithm can be an algorithm selected from algorithms A1 to A8 to be described later, and the second algorithm can be an algorithm selected from algorithms A1 to A8 other than the first algorithm.

In step S801, the processor 240 determines whether a first event for updating the presence/absence of the aerosol source is detected. The first event can be pressing of a power supply button or a remaining amount display button (neither are shown), an atomization request, or the like. If the first event is detected, the process advances to step S802. If the first event is not detected, the process advances to step S805.

In step S802, the processor 240 acquires a first parameter that is a variable necessary for executing the first determination processing. In step S803, the processor 240 executes the first determination processing by the first algorithm using the first parameter acquired in step S802. In step S804, the processor 240 determines whether the result of the first determination processing represents aerosol source absence (that is, exhaustion). Upon determining aerosol source absence, the process advances to step S809, and the processor 240 inhibits feeding to the heater 127, thereby inhibiting generation of an aerosol. Next, in step S810, the processor 240 updates the remaining amount stored in the memory to 0.

On the other hand, upon determining aerosol source presence in step S804, the process advances to step S805. In step S805, the processor 240 determines whether a second event for updating the presence/absence of the aerosol source is detected. The second event can be, for example, an atomization request. If the second event is detected, the process advances to step S806. If the second event is not detected, this operation is ended.

In step S806, the processor 240 acquires a second parameter that is a variable necessary for executing the second determination processing. In step S807, the processor 240 executes the second determination processing by the second algorithm using the second parameter acquired in step S806. In step S808, the processor 240 determines whether the result of the second determination processing represents aerosol source absence (that is, exhaustion). Upon determining aerosol source absence, the process advances to step S809, and the processor 240 inhibits feeding to the heater 127, thereby inhibiting generation of an aerosol. Next, in step S810, the processor 240 updates the remaining amount stored in the memory to 0. If aerosol source presence is determined in step S808, this is a case in which exhaustion is not detected by the first determination processing and the second determination processing, and this operation is ended.

As described above, according to this operation example, if aerosol source absence is determined by one of the first determination processing and the second determination processing, and aerosol source presence is determined by the other of the first determination processing and the second determination processing, supply of power to the heater 127 is inhibited. This can reliably suppress a situation in which the atomization operation (heating of the heater 127) is continuously performed despite of the exhaustion of the aerosol source in the atomizer 104. It is also possible to reliably suppress generation of an undesirable flavor.

In each of the above-described operation examples, at least a part of the timing of executing the first determination processing is different from the timing of executing the second determination processing. This makes it possible to provide the information of the presence/absence or the remaining amount of the aerosol source, which is as latest as possible, to the user. Additionally, in each operation example, the variable necessary for executing the first determination processing and the variable necessary for executing the second determination processing are different. For this reason, even if a determination error has occurred in one of the first determination processing and the second determination processing, the determination error can be compensated for by the other. It is therefore possible to obtain an accurate determination result.

<Examples of Algorithms for Determining Presence/Absence or Remaining Amount of Aerosol Source>

Various algorithms can be employed as the first algorithm concerning the first determination processing and the second algorithm concerning the second determination processing in each of the above-described operation examples. Examples of the algorithms for determining the presence/absence or the remaining amount of the aerosol source will be described below. In the following description, the algorithms A1 to A8 are algorithms for determining the presence/absence of the aerosol source, and the algorithms B1 to B6 are algorithms for determining the remaining amount of the aerosol source.

(Algorithm A1)

The algorithm A1 determines the presence/absence of the aerosol source based on the temperature of the heater 127 (to be referred to as a heater temperature hereinafter) or the rising speed of the heater temperature. In the algorithm A1, the variable (parameter) necessary for determining the presence/absence of the aerosol source is the resistance value $R_{HTR}$ of the heater 127 or the heater temperature.

In an example, upon receiving an atomization request, the processor 240 detects the resistance value $R_{HTR}$ of the heater 127. More specifically, in a state in which the switch SW1 is off, and the switch SW2 is on, the processor 240 calculates the resistance value $R_{HTR}$ of the heater 127 in accordance with equations (2) and (4) based on the output voltage $V_{AMP}$ of the amplifier AMP of the detection circuit 220. Next, the processor 240 calculates the temperature $T_{HTR}$ of the heater 127 in accordance with equation (5) based on the calculated resistance value $R_{HTR}$ of the heater 127 and the reference temperature $T_{ref}$ and the reference resistance value $R_{ref}$, which are set in advance.

After that, the processor 240 determines whether the calculated temperature $T_{HTR}$ of the heater 127 exceeds a predetermined threshold (for example, 250° C.). Note that the threshold can be determined in accordance with the type of the aerosol source, the structure of the transporter 126, and the like. If the temperature $T_{HTR}$ exceeds the threshold, the processor 240 determines aerosol source absence (that is, exhaustion) representing that the aerosol source in (the container 125 of) the atomizer 104 is absent. If the temperature $T_{HTR}$ does not exceed the threshold, the processor 240 determines aerosol source presence.

A temperature profile representing the change of the heater temperature relative to the heater heating (feeding) duration changes between a case in which the remaining amount of the aerosol source is sufficient and a case in which the aerosol source is exhausted. It is known that the rising speed of the heater temperature is higher in the case in which the aerosol source is exhausted than in the case in which the remaining amount of the aerosol source is sufficient. In another example, upon receiving the atomization request, the processor 240 calculates the heater temperature at each of a first time during heating of the heater 127 and a second time after a predetermined time from the first time, and calculates the rising speed (change rate) of the heater temperature.

After that, the processor 240 determines whether the calculated rising speed exceeds a predetermined threshold. If the rising speed exceeds the threshold, aerosol source absence is determined. If the rising speed does not exceed the threshold, aerosol source presence is determined.

(Algorithm A2)

The algorithm A2 determines the presence/absence of the aerosol source based on the change rate of the resistance value $R_{HTR}$ of the heater 127. In the algorithm A2, the variable (parameter) necessary for determining the presence/absence of the aerosol source is the resistance value $R_{HTR}$ of the heater 127 or the heater temperature.

Upon receiving the atomization request, the processor 240 detects the resistance value $R_{HTR}$ of the heater 127 at each of a first time during heating of the heater 127 and a second time after a predetermined time from the first time, and calculates the change rate of the resistance value $R_{HTR}$ of the heater 127. After that, the processor 240 determines whether the calculated change rate exceeds a predetermined threshold. If the change rate exceeds the threshold, aerosol source absence is determined. If the change rate does not exceed the threshold, aerosol source presence is determined.

(Algorithm A3)

The algorithm A3 determines the presence/absence of the aerosol source based on an index associated with a variation of the heater temperature in each feed cycle. In the algorithm A3, the variable (parameter) necessary for determining the presence/absence of the aerosol source is the resistance value $R_{HTR}$ of the heater 127 or the heater temperature.

One feed cycle is a period corresponding to the period (puff period) of one inhalation operation, and can be, for example, a feed period from reception of an atomization request by the processor 240 to the end of the atomization request. As described above, a temperature profile representing the change of the heater temperature relative to the heater heating (feeding) duration changes between a case in which the remaining amount of the aerosol source is sufficient and a case in which the aerosol source is exhausted. Here, in the temperature profile in the case in which the remaining amount of the aerosol source is sufficient, the heater temperature converges to a value close to a temperature corresponding to the boiling point of the aerosol source transported by the transporter 126 to the heating area of the heater 127. On the other hand, in the temperature profile in the case in which the aerosol source is exhausted, the variation (fluctuation) of the heater temperature is larger than in the case in which the remaining amount of the aerosol source is sufficient because of the absence of supply of the aerosol source, and the like. It is therefore possible to determine the presence/absence of the aerosol source by the magnitude of the variation of the heater temperature.

Upon receiving an atomization request, the processor 240 repetitively detects the resistance value $R_{HTR}$ of the heater 127, calculates the heater temperature based on the resistance value $R_{HTR}$, and stores the heater temperature in the memory until the end of the atomization request. The data of the heater temperature in one feed cycle can thus be obtained. Next, the processor 240 calculates an index (for example, a standard deviation) associated with the variation of the heater temperature in the feed cycle. At this time, data processing of excluding the data of the heater temperature during the temperature rising period or in the early stage of the feed cycle from the calculation target may be performed.

After that, the processor 240 determines whether the calculated index exceeds a predetermined threshold. If the index does not exceed the threshold, aerosol source absence is determined. If the index exceeds the threshold, aerosol source presence is determined.

(Algorithm A4)

The algorithm A4 determines the presence/absence of the aerosol source based on an index associated with a variation of the heater temperature in each of two latest feed cycles. In the algorithm A4, the variable (parameter) necessary for determining the presence/absence of the aerosol source is the resistance value $R_{HTR}$ of the heater 127 or the heater temperature.

By an operation similar to the above-described algorithm A3, the processor 240 acquires the data of the heater temperature in a first feed cycle and the data of the heater temperature in a second feed cycle next to the first feed cycle, and calculates a first index (for example, a standard deviation) associated with the variation of the heater temperature in the first feed cycle and a second index (for example, a standard deviation) associated with the variation of the heater temperature in the second feed cycle. At this time, data processing of excluding the data of the heater temperature during the temperature rising period or in the early stage of the feed cycle from the calculation target may be performed.

For example, the processor 240 determines, based on the first index, whether the heater temperature in the first feed cycle is in a steady state (high-temperature steady state) at a temperature higher than the heater temperature in a case in which the remaining amount of the aerosol source is sufficient. In addition, the processor 240 determines, based on the second index, whether the heater temperature in the second feed cycle is also in the high-temperature steady state. Upon determining that both the heater temperature in the first feed cycle and the heater temperature in the second feed cycle are in the high-temperature steady state, the processor 240 determines aerosol source absence. Otherwise, the processor 240 determines aerosol source presence.

(Algorithm A5)

The algorithm A5 determines the presence/absence of the aerosol source based on the cooling speed or the cooling time of the heater temperature after the end of aerosol generation. In the algorithm A5, the variable (parameter) necessary for determining the presence/absence of the aerosol source is the resistance value $R_{HTR}$ of the heater 127 or the heater temperature.

Upon receiving an atomization request, the processor 240 performs feeding to the heater 127, and after the end of the atomization request, stops feeding to the heater 127. The heater temperature lowers along with the elapse of time by natural cooling of the heater 127, and converges to a temperature corresponding to room temperature. However, if the aerosol source is exhausted, the heater temperature is higher than in a case in which the remaining amount of the aerosol source is sufficient, and the heater 127 is not cooled by the aerosol source transported from the transporter 126, the cooling speed is low, and a long time is needed until the heater temperature converges to a temperature corresponding to room temperature.

In an example, upon receiving an atomization request, the processor 240 performs feeding to the heater 127, stops feeding to the heater 127 after the end of the atomization request, detects the resistance value $R_{HTR}$ of the heater 127, and calculates a heater temperature T1. Also, after the elapse of a predetermined time Δt, the processor 240 detects the resistance value $R_{HTR}$ of the heater 127, and calculates a heater temperature T2. Next, the processor 240 calculates a cooling speed S=(T1−T2)/Δt of the heater 127.

After that, the processor 240 determines whether the calculated cooling speed exceeds a predetermined threshold. If the cooling speed does not exceed the threshold, aerosol source absence is determined. If the cooling speed exceeds the threshold, aerosol source presence is determined.

In another example, upon receiving an atomization request, the processor 240 performs feeding to the heater 127, stops feeding to the heater 127 after the end of the atomization request, activates a timer, detects the resistance value $R_{HTR}$ of the heater 127, calculates the heater temperature, and determines whether the calculated heater temperature is equal to or lower than a threshold temperature corresponding to room temperature. The processor 240 repeats the calculation of the heater temperature in each unit time until the heater temperature becomes equal to or lower than the threshold temperature, and measures the timer value at the point of time when the heater temperature has become equal to or lower than the threshold temperature. The cooling time of the heater 127 is thus measured.

After that, the processor 240 determines whether the measured cooling time exceeds a predetermined threshold. If the cooling time exceeds the threshold, aerosol source absence is determined. If the cooling speed does not exceed the threshold, aerosol source presence is determined.

(Algorithm A6)

The algorithm A6 determines the presence/absence of the aerosol source based on the resistance value after the heater 127 is heated and cooled. That is, in the algorithm A6, the variable (parameter) necessary for determining the presence/absence of the aerosol source is the resistance value $R_{HTR}$ of the heater 127.

In a case in which the aerosol source is sufficient, if the temperature of the heater 127 reaches the maximum temperature of the aerosol source (for example, 200° C.) to be reached in a normal state, the resistance value of the heater 127 does not increase anymore. After that, when the atomization request ends, and feeding to the heater 127 is stopped, the temperature of the heater 127 lowers, and the resistance value of the heater 127 also lowers. When the temperature of the heater 127 reaches room temperature, the resistance value returns to the value before heating of the heater 127.

On the other hand, if the aerosol source is exhausted, the temperature of the heater 127 exceeds the maximum temperature of the aerosol source to be reached in the case in which the remaining amount of the aerosol source is sufficient, and further rises to a temperature (for example, 350° C.) reachable only at the time of exhaustion of the aerosol source. Here, a material whose physical property (changes the electrical resistance value change) when reaching the temperature reachable only at the time of exhaustion of the aerosol source is used in the heater 127. An example of the change of the physical property is formation of an oxidized film on the surface of the heater 127. When the atomization request ends, and feeding to the heater 127 is stopped, the temperature of the heater 127 lowers, and the resistance value of the heater 127 also lowers. However, since the physical property of the heater 127 changes from that before heating, the resistance value of the heater 127 does not return to the value before heating even if the temperature of the heater 127 returns to room temperature. Hence, the converged value of the resistance value of the heater 127 changes depending on whether the aerosol source is exhausted.

When holding of the atomizer 104 by the holder 103 is detected, the processor 240 detects the resistance value $R_{HTR}$ of the heater 127. Upon receiving an atomization request, the processor 240 performs feeding to the heater 127. After that, when the atomization request ends, the processor 240 stops feeding to the heater 127, activates the timer, and waits for the elapse of a cooling time determined in advance as a sufficient time for the heater temperature to return to room temperature. After the elapse of the cooling time, the processor 240 detects a resistance value $R'_{HTR}$ of the heater 127 after heating/cooling. Next, the processor 240 determines whether the difference between the resistance value $R'_{HTR}$ of the heater 127 after heating/cooling and the initial resistance value $R_{HTR}$ is larger than a predetermined threshold. If the difference is larger than the threshold, aerosol source absence is determined. If the difference is not larger than the threshold, aerosol source presence is determined.

(Algorithm A7)

If a sensor including a rigid resistance line embedded in the transporter 126 is provided, the presence/absence of the aerosol source can be determined based on the electrical resistance value of the rigid resistance line. Hence, in the algorithm A7, the variable (parameter) necessary for determining the presence/absence of the aerosol source is the resistance value of the rigid resistance line embedded in the transporter 126.

Upon receiving an atomization request, the processor 240 detects the resistance value of the rigid resistance line embedded in the transporter 126. Next, the processor 240 determines whether the detected resistance value exceeds a predetermined threshold. If the resistance value exceeds the threshold, aerosol source absence is determined. If the resistance value does not exceed the threshold, aerosol source presence is determined.

(Algorithm A8)

If a temperature sensor configured to detect the temperature of the aerosol source in the container 125 is arranged in the container 125, the presence/absence of the aerosol source can be determined based on the temperature detected by the temperature sensor. Hence, in the algorithm A8, the variable (parameter) necessary for determining the presence/absence of the aerosol source is the temperature detected by the temperature sensor arranged in the container 125.

Upon receiving an atomization request, the processor 240 acquires the temperature detected by the temperature sensor arranged in the container 125. Next, the processor 240 determines whether the acquired temperature exceeds a predetermined threshold. If the temperature exceeds the threshold, aerosol source absence is determined. If the temperature does not exceed the threshold, aerosol source presence is determined.

<Examples of Algorithms for Determining Remaining Amount of Aerosol Source>

(Algorithm B1)

If the relationship (atomization characteristic) between the inhalation time and the atomization amount is known, the consumption amount of the aerosol source can be estimated based on the cumulative inhalation time. Hence, the algorithm B1 determines the remaining amount of the aerosol source based on the ratio of the current cumulative inhalation time to the cumulative inhalation time upper limit value (corresponding to the full amount of the aerosol source). In the algorithm B1, the variable (parameter) necessary for determining the remaining amount of the aerosol source is the inhalation time in each inhalation operation. Note that if an upper limit time to perform feeding to the heater 127 in one inhalation operation is determined in advance, the time in which feeding is actually performed may be used in place of the inhalation time.

Upon receiving an atomization request, the processor 240 performs feeding to the heater 127 and activates a timer, and stops feeding to the heater 127 in accordance with the end of the atomization request, stops the timer, and measures the timer value. The inhalation time in one inhalation operation is thus specified. In every inhalation operation, the cumulative value of the measured timer value is stored in the memory, thereby acquiring the cumulative inhalation time. In every inhalation operation, the processor 240 calculates the remaining amount of the aerosol source based on the acquired cumulative inhalation time.

Note that strictly speaking the relationship between the inhalation time and the atomization amount is not linear. This is because there is a time delay from the start of feeding to the heater 127 to stabilization of the heater temperature. In addition, since the initial temperature of the heater 127 at the start of feeding to the heater 127 changes depending on the time interval (inhalation operation interval) from the end of the previous inhalation operation, the time delay from the start of feeding to the heater 127 to stabilization of the heater temperature also changes. Hence, the processor 240 may correct the inhalation time or the cumulative inhalation time based on the timer value and/or the inhalation operation interval measured in every inhalation operation.

(Algorithm B2)

The algorithm B2 determines the remaining amount of the aerosol source based on the heater temperature or the increase rate of the heater temperature. In the algorithm B2, the variable (parameter) necessary for determining the remaining amount of the aerosol source is the resistance value $R_{HTR}$ of the heater 127 or the heater temperature. If a temperature sensor configured to detect the temperature of the heater 127 is arranged, the variable (parameter) necessary for determining the remaining amount of the aerosol source can be the heater temperature detected by the temperature sensor.

In an example, upon receiving an atomization request, the processor 240 detects the resistance value $R_{HTR}$ of the heater 127. Next, the processor 240 calculates the heater temperature based on the calculated resistance value $R_{HTR}$ of the heater 127. After that, the processor 240 acquires the remaining amount of the aerosol source corresponding to the calculated heater temperature based on the relationship between the heater temperature and the remaining amount of the aerosol source, which is obtained in advance.

The algorithm B2 may determine the remaining amount of the aerosol source based on the rising speed of the heater temperature. In this case, upon receiving an atomization request, the processor 240 calculates the heater temperature at each of a first time during heating of the heater 127 and a second time after a predetermined time from the first time, and calculates the rising speed (change rate) of the heater temperature.

After that, the processor 240 acquires the remaining amount of the aerosol source corresponding to the calculated rising speed based on the relationship between the rising speed of the heater temperature and the remaining amount of the aerosol source, which is obtained in advance.

(Algorithm B3)

If a temperature profile representing the change of the heater temperature relative to the heater heating (feeding) duration is known, and the characteristic of the atomization rate to the heater temperature is known, an atomization rate profile representing the change of the atomization rate to the heater heating duration can be obtained. The algorithm B3 determines the remaining amount of the aerosol source based on the atomization rate profile.

Upon receiving an atomization request, the processor 240 performs feeding to the heater 127 and activates a timer, and stops feeding to the heater 127 in accordance with the end of the atomization request, stops the timer, and measures the timer value. The inhalation time in one inhalation operation is thus specified. The processor 240 performs integration under an atomization rate curve in the specified inhalation time, thereby acquiring the atomization amount, that is, the consumption amount of the aerosol source in the inhalation time. In every inhalation operation, the acquired cumulative value of the consumption amount of the aerosol source is stored in the memory, thereby acquiring the cumulative consumption amount of the aerosol source. In every inhalation operation, the processor 240 subtracts the acquired cumulative consumption amount of the aerosol source from the full amount value of the aerosol source that can be held in the container 125, thereby acquiring the remaining amount of the aerosol source.

(Algorithm B4)

The algorithm B4 determines the remaining amount of the aerosol source based on the electrical resistance value of the transporter 126. In the algorithm B4, the variable (parameter) necessary for determining the remaining amount of the aerosol source is the electrical resistance value of the transporter 126.

Upon receiving an atomization request, the processor 240 detects the electrical resistance value of the transporter 126. After that, the processor 240 acquires the remaining amount of the aerosol source corresponding to the calculated electrical resistance value of the transporter 126 based on the relationship between the electrical resistance value of the transporter 126 and the remaining amount of the aerosol source, which is obtained in advance.

(Algorithm B5)

Here, an electrode arranged at a first position in the container 125 and an electrode arranged at a second position apart from the first position in the container 125 are connected to the detection circuit 220, and the detection circuit 220 is configured to detect the electrical resistance value between the electrodes in the container 125. The electrical resistance value between the electrodes changes depending on the filling state of the aerosol source in the container 125. For example, in a state in which the container 125 is filled with the aerosol source, the electrical resistance value is low. The electrical resistance value becomes high along with a decrease in the aerosol source in the container 125.

The algorithm B5 determines the remaining amount of the aerosol source based on the electrical resistance value between the electrodes in the container 125. Hence, in the algorithm B5, the variable (parameter) necessary for determining the remaining amount of the aerosol source is the electrical resistance value between the electrodes in the container 125.

Upon receiving an atomization request, the processor 240 detects the electrical resistance value between the electrodes in the container 125. After that, the processor 240 acquires the remaining amount of the aerosol source corresponding to the detected electrical resistance value based on the relationship between the electrical resistance value between the electrodes and the remaining amount of the aerosol source, which is obtained in advance.

Alternatively, in a state in which the container 125 is filled with the aerosol source, the variation (fluctuation) of the electrical resistance value is small. The variation of the electrical resistance value becomes large along with a decrease in the aerosol source in the container 125. In another example, upon receiving an atomization request, the processor 240 detects the electrical resistance value between the electrodes in the container 125 a plurality of times, and calculates an index concerning the variation of the detected electrical resistance values. After that, the processor 240 acquires the remaining amount of the aerosol source corresponding to the index concerning the variation of the electrical resistance value obtained by calculation based on the relationship between the index concerning the variation of the electrical resistance value between the electrodes and the remaining amount of the aerosol source, which is obtained in advance.

(Algorithm B6)

Here, an electrode arranged at a first position in the container 125 and an electrode arranged at a second position apart from the first position in the container 125 are connected to the detection circuit 220, and the detection circuit 220 is configured to detect the electrostatic capacitance between the electrodes in the container 125. The electrostatic capacitance between the electrodes changes depending on the filling state of the aerosol source in the container 125. For example, in a state in which the container 125 is filled with the aerosol source, the electrostatic capacitance is large. The electrostatic capacitance becomes small along with a decrease in the aerosol source in the container 125.

The algorithm B6 determines the remaining amount of the aerosol source based on the electrostatic capacitance between the electrodes in the container 125. Hence, in the algorithm B6, the variable (parameter) necessary for determining the remaining amount of the aerosol source is the electrostatic capacitance between the electrodes in the container 125.

Upon receiving an atomization request, the processor 240 detects the electrostatic capacitance between the electrodes in the container 125. After that, the processor 240 acquires the remaining amount of the aerosol source corresponding to the detected electrostatic capacitance based on the relationship between the electrostatic capacitance between the electrodes and the remaining amount of the aerosol source, which is obtained in advance.

Alternatively, in a state in which the container 125 is filled with the aerosol source, the variation (fluctuation) of the electrostatic capacitance is small. The variation of the electrostatic capacitance becomes large along with a decrease in the aerosol source in the container 125. In another example, upon receiving an atomization request, the processor 240 detects the electrostatic capacitance between the electrodes in the container 125 a plurality of times, and calculates an index concerning the variation of the detected electrostatic capacitances. After that, the processor 240 acquires the remaining amount of the aerosol source corresponding to the index concerning the variation of the electrostatic capacitance obtained by calculation based on the relationship between the index concerning the variation of the electrostatic capacitance between the electrodes and the remaining amount of the aerosol source, which is obtained in advance.

Various examples of the algorithms configured to determine the presence/absence or the remaining amount of the aerosol source have been described above. The above-described algorithms are merely examples, and algorithms other than these may be employed.

As described in the above examples of the algorithms, the variable necessary for executing the first determination processing can be acquired from one element of the heater 127, the container 125, and the transporter 126 in accordance with the first algorithm employed in the first determination processing. At this time, the variable necessary for executing the second determination processing is preferably acquired from one of the heater 127, the container 125, and the transporter 126 other than the element in accordance with the second algorithm employed in the second determination processing. In this case, since the observation target changes between the first determination processing and the second determination processing, for example, even if the product error or the like of one observation target is large, the observation error in the one determination processing can be compensated for by determination processing using the other observation target. It is therefore possible to obtain an accurate determination result.

The invention is not limited to the foregoing embodiments, and various variations/changes are possible within the spirit of the invention.

What is claimed is:

1. An inhalation device controller comprising:
   a holder configured to hold an atomizer including a heater for atomizing an aerosol source; and
   a processor configured to execute, upon detecting an atomization request, first determination processing of determining a remaining amount of the aerosol source in the atomizer held by the holder using a first algorithm, and execute, upon detecting an atomization request after the execution of the first determination processing, second determination processing of determining presence/absence of the aerosol source in the atomizer using a second algorithm different from the first algorithm, and control a supply of power to the heater; and
   a memory configured to store a value of the remaining amount of the aerosol source in the atomizer,
   wherein even if it is determined by the first determination processing that the remaining amount is larger than 0, if aerosol source absence is determined by the second determination processing, the processor outputs the aerosol source absence as a final determination result, and inhibits the supply of power to the heater and updates the value in the memory to 0 according to the final determination result.

2. An inhalation device controller comprising:
   a holder configured to hold an atomizer including a heater for atomizing an aerosol source; and
   a processor configured to execute, upon detecting an atomization request, first determination processing of determining presence/absence of the aerosol source in the atomizer using a first algorithm, and execute, only if aerosol presence is determined by the first determination processing, a second determination processing of determining a remaining amount of the aerosol source in the atomizer using a second algorithm different from the first algorithm.

3. The controller according to claim 1, wherein the atomizer further comprises a container configured to hold the aerosol source, and a transporter configured to transport the aerosol source in the container to a position at which the aerosol source can be heated by the heater,
   a variable necessary for executing the first determination processing is acquired from one element of the heater, the container, and the transporter, and
   a variable necessary for executing the second determination processing is acquired from one of the heater, the container, and the transporter other than the element.

4. An inhalation device controller comprising:
   a holder configured to hold an atomizer including a heater for atomizing an aerosol source; and a processor configured to execute first determination processing of determining one of presence/absence and a remaining amount of the aerosol source in the atomizer held by the holder using a first algorithm, and second determination processing of determining one of the presence/absence and the remaining amount using a second algorithm different from the first algorithm, wherein the atomizer further comprises a container configured to hold the aerosol source, and a transporter configured to transport the aerosol source in the container to a position at which the aerosol source can be heated by the heater, a variable necessary for executing the first determination processing is acquired from one element of the heater, the container, and the transporter, and a variable necessary for executing the second determination processing is acquired from one of the heater, the container, and the transporter other than the element.

* * * * *